United States Patent [19]

Pierce

[11] 4,282,181
[45] Aug. 4, 1981

[54] ACCELERATED CORROSION TEST APPARATUS

[75] Inventor: Danny A. Pierce, Columbus, Ohio

[73] Assignee: IPM Corporation, Columbus, Ohio

[21] Appl. No.: 968,056

[22] Filed: Dec. 11, 1978

[51] Int. Cl.³ ............................................. G01N 17/00
[52] U.S. Cl. .................................... 422/53; 73/432 SD
[58] Field of Search ....................... 422/53; 73/432 SD

[56] References Cited

U.S. PATENT DOCUMENTS

| 3,116,977 | 1/1964 | Grabowski et al. | 422/53 X |
| 3,936,273 | 2/1976 | Powell | 422/53 |

OTHER PUBLICATIONS

Crampton et al., "Alternate Immersion and Water—Line Tests", Amer. Soc. Testing Materials, Symposium on Corrosion Testing Procedures, 1937, pp. 74–86.
Champion, "Corrosion Testing Procedures—2nd Edition," John Wiley & Sons Inc., New York, 1965, pp. 59–83, Scientific Library TA 462 C441965.

*Primary Examiner*—Arnold Turk
*Attorney, Agent, or Firm*—William J. O'Rourke, Jr.

[57] ABSTRACT

An apparatus for the accelerated testing of the corrosion resistance of a plurality of parts in an isolated environment is disclosed including a horizontally disposed support bar from which the parts to be tested depend. A reservoir of corrosive liquid media is located vertically below the support bar and a drying zone is located above the reservoir wherein the temperature is controlled within plus or minus 10° C. The test unit is operated by reciprocally driving the support bar such that when the bar is in its lowermost position the parts are immersed in liquid corrosive media and when the bar is in its uppermost position the parts are in the temperature controlled drying zone. Controls are also provided to selectively retain the parts in the corrosive media and in the drying zone for predetermined, repetitive periods of time.

1 Claim, 2 Drawing Figures

ACCELERATED CORROSION TEST APPARATUS

BACKGROUND OF THE INVENTION

1. Field of the Invention

The present invention relates to testing apparatus and more particularly to an improved apparatus for the accelerated testing of the corrosion resistance of a plurality of parts under exacting repetitive conditions.

2. Description of the Art

The industry of precision powder metallurgical parts, including structural components, and plated parts has experienced significant growth over the past decade. As a result of such growth especially into areas where the use of such parts is critical, quality control of the manufacturing process has become increasingly important.

An exemplary quality control application for such parts is the testing of corrosion resistance. Testing a part for corrosion resistance in its actual operating environment is too time consuming to provide the rapid feedback necessary to effectively control quality.

It has been found that corrosion resistance may be determined relatively quickly by an accelerated test involving repetitive immersion of a part in a corrosive liquid following intermittent drying of the part. A known apparatus which may be used for repetitively immersing a part in liquid corrosive media is a rotary Ferris wheel type design in which the parts to be tested are placed in individual baskets located around the periphery of the wheel. The wheel is located over a corrosive bath such that the part is immersed in the corrosive media as each basket passes through its lower area of rotation. The part comes out of the bath as the basket is moved upwardly upon continued rotation of the wheel. Shortcomings of this type of apparatus include the necessity of constructing a reservoir with sufficient size to accommodate the rotary path of the baskets. Also, the time of immersion is necessarily related to the drying time as both are functions of the depth of the bath and the wheel speed. For example, increasing the time of immersion, by reducing the speed of the wheel, causes a corresponding increase in the drying time. Likewise, increasing the wheel speed to decrease the time of immersion of a part results in a decrease in the drying time. Further, the same reservoir of corrosive liquid must necessarily be used for all parts in the test, while it is often desirable to test the similar parts from the same stock in a plurality of corrosive liquids. Also, with a wheel type design corrosives may drip from one part, or basket, to another part located therebelow sometimes affecting the test results.

The American Society for Testing Materials (ASTM) has published specifications for detecting the susceptibility to intergranular attack in molybdenum bearing stainless steels, see ASTM Test No. A262, Practice D. The apparatus described for conducting such test includes polyvinyl chloride cylinders, specimen holders and a constant temperature acidic bath. The prepared specimens are supported in the cylinder and the cylinder is filled with acid solution and heated. After adequate exposure to the solution the specimens are removed.

A variety of other test apparatus are known in the art which include baskets in which a plurality of parts are stacked for simultaneous immersion into a corrosive bath. Such apparatus require immersion of all of the parts into the same bath. A drawback of this system is that if the common bath becomes contaminated, the entire test procedure may have to be repeated. Also such apparatus may exhibit drainage problems when the residual bath on the upper or adjacent stacked parts drains over the lower or adjacent stacked parts as the basket is removed for drying of the parts.

An apparatus for simultaneously raising and lowering a plurality of parts into liquid corrosive media is also known in which the parts are repeatedly immersed and dried. Drying in such apparatus is accomplished by a plurality of heat lamps located adjacent the apparatus. In addition to the heat lamps being separate from the unit, such apparatus has separate power controls which, when installed, limit the portability thereof. Further, the apparatus does not include an isolated environment in which the repetitive test procedure is isolated from the ambient atmosphere. Furthermore, heat lamps do not provide a temperature in a heating or drying zone that can be tightly controlled to yield extremely accurate and comparative test results as may be required in certain corrosion test applications. Also, such apparatus does not enhance unobstructed visual inspection of the parts at any stage of the repetitive test.

For corrosion resistance tests to yield accurate measurements which are valuable for comparison purposes all test criteria, including immersion time, drying time, drying temperature, and isolation from the ambient environment must be maintained and controlled within tight tolerances. For example, no technician can accurately position a test sample on a repetitive manual basis with any degree of consistency. Manual testing tends to yield inaccurate results because of the inability to repeat dipping of a test sample at the same angle, depth or time with each repetitive cycle. The same inaccuracies are found in various, prior art drying devices. The necessity for control is especially true when considering that adequate accelerated corrosion tests require relatively long test periods on the order of eight hours. It is important to repeat the steps of the accelerated corrosion test under as exact repetitive conditions as is possible in order to obtain meaningful comparative data.

Accordingly an accelerated corrosion test apparatus is desired which is able to determine the corrosion resistance of a plurality of parts by testing such parts in a controlled environment to yield more accurate results than test apparatus known heretofore. Ideally, such apparatus shall provide the industry with a unit which is able to control corrosion test parameters sufficient to establish a commercially acceptable standard corrosion testing apparatus.

SUMMARY OF THE INVENTION

The present invention may be summarized as providing an improved apparatus for the accelerated testing of the corrosion resistance of a plurality of parts in an isolated environment. This apparatus includes a horizontally disposed support bar from which the parts to be tested depend. A reservoir of corrosive liquid media is located vertically below the support bar and a drying zone is located vertically above the reservoir wherein the temperature is controlled within plus or minus 10° C. The test unit is operated by reciprocally driving the support bar while the bar is maintained in a substantially horizontal position such that when the bar is in its lowermost position the parts are immersed in liquid corrosive media and when the bar is in its uppermost position the parts are in the temperature controlled drying zone. Controls are also provided to selectively retain the parts in the corrosive media and in the drying zone for predetermined, repetitive periods of time.

An objective of this invention is to provide an apparatus in which a plurality of test samples are repetitively dipped in a corrosive media and dried thereby concentrating the corrosive media and accelerating crevice type corrosion.

Among the advantages of the present invention is the provision of an apparatus which is able to test accurately and consistently the corrosion resistance of a plurality of parts.

A primary objective of this invention is to provide an apparatus which is able to control accelerated corrosion testing parameters to such tight tolerances, and under such exacting conditions that the unit comes to be used as a commercially acceptable, standard apparatus for testing corrosion throughout the industry.

Another advantage of this invention is to provide an apparatus in which a plurality of parts may be simultaneously tested for corrosion resistance in a variety of corrosive liquids.

A further advantage of the present invention is to provide an apparatus in which finished parts may be simultaneously tested with and compared to standard tests specimens.

An objective of this invention is to provide an apparatus which effectively controls the repetitive dipping and drying of the parts under test to insure uniformity in terms of dip time, dry time and dry temperature with each repetitive test cycle.

Another objective of this invention is to provide a generally portable accelerated corrosion test apparatus which would not occupy excessive space, or require elaborate external controls or semi-permanent connections in a testing laboratory.

A further objective of this invention is to provide an apparatus which automatically operates over prolonged periods of time and under exacting repetitive conditions without the need for monitoring the testing process between the starting and stopping steps, yet permits visual observation and inspection of the parts being tested during operating, without having to interrupt the operation of the apparatus.

These and other objectives and advantages of this invention will be more fully understood and appreciated with reference to the following detailed description and the drawings appended hereto.

DESCRIPTION OF THE PREFERRED EMBODIMENTS

Figure 1:
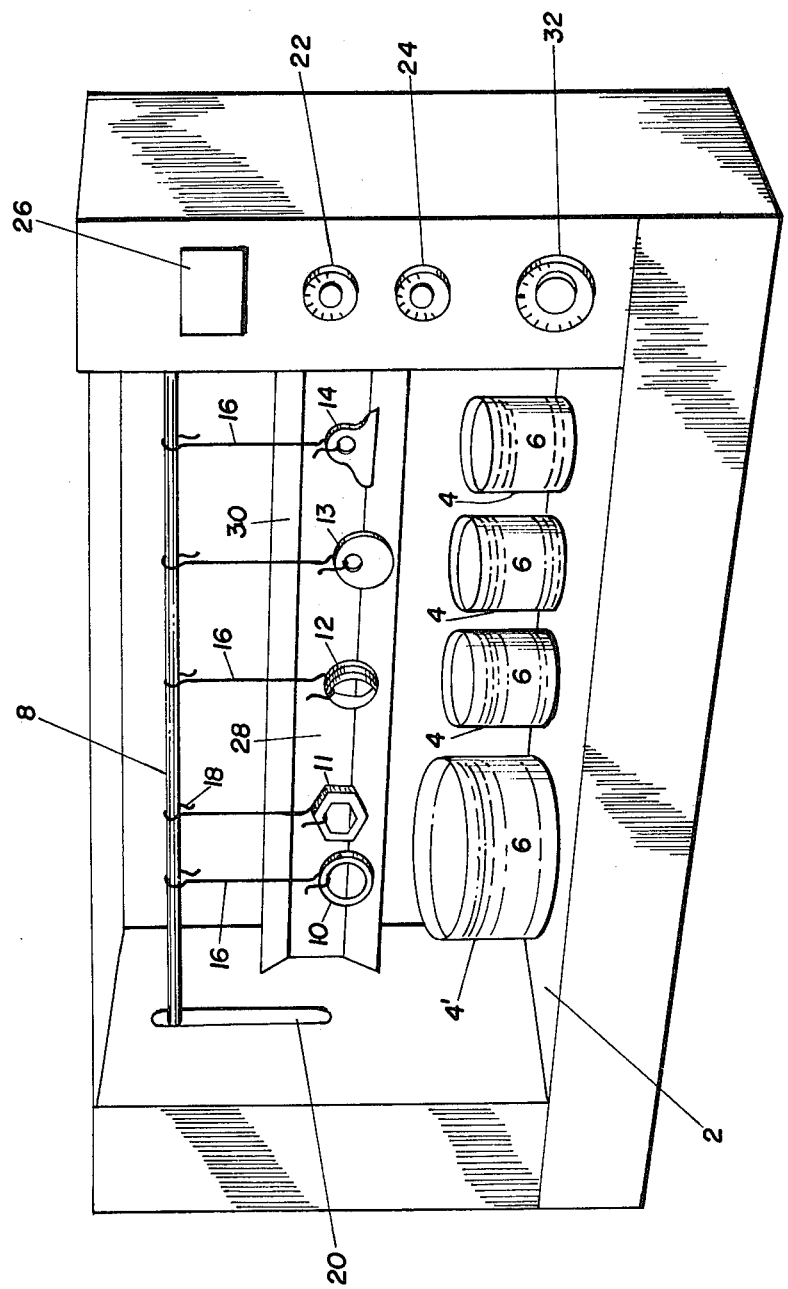
FIG. 1 is a perspective view of the apparatus of the present invention showing the parts in the drying zone.

Referring particularly to the drawings, FIG. 1 illustrates a preferred apparatus of the present invention for simultaneously testing the corrosion resistance of a plurality of parts on an accelerated basis under exact repetitive conditions. The apparatus includes a base 2 upon which the reservoir 4 of corrosive media 6 is located. In an alternative embodiment the base 2 may be provided with a plurality of recesses in which the corrosive liquid media 6 may be located, or in which reservoirs 4 may be positioned to assure that their position is not altered as may otherwise occur with normal handling of the machine, relocation and refilling of the reservoirs and in the routine operation of the apparatus. In another embodiment, a heating element may be provided on or in the base 2, where it may be necessary or desirable to maintain a certain temperature for the corrosive liquid media 6 in the reservoir 4.

In a preferred embodiment, as illustrated in the drawing the reservoir 4 of corrosive liquid media 6 consists of a glass beaker. Glass is chosen for its nonreactive qualites as well as for its resistance to the common corrosive liquids such as a one percent aqueous sodium chloride solution. Glass beakers are also readily available and relatively inexpensive. A plurality of standard 250 milliliter beakers may be used in the testing apparatus. When such 250 ml beakers are employed each beaker usually accommodates the testing of only one part per beaker. Thus, common parts from the same stock may be simultaneously tested in several corrosive solutions, or in identical corrosive solutions as desired. Alternatively, larger beakers or other nonreactive, corrosion resistant containers or receptacles may be employed to readily accommodate the testing of a plurality of parts into a common bath. As illustrated in FIG. 1 reservoir 4' is larger in cross sectional dimension than the other reservoirs 4 shown. Such a reservoir 4' allows a plurality of parts to be immersed into the common bath 6' during testing as explained in more detail below.

Although the base 2 need not be perfectly level it is preferred that the base not be disposed more than a few degrees from horizontal. It is necessary that the base 2 be disposed such that the reservoir 4 thereon or therein may be provided with corrosive liquid media 6 and permit immersion of the parts to be tested.

A support bar 8 is disposed vertically above the base 2 and the reservoirs 4. The support bar 8 lies substantially in the horizontal position. By "substantially in the horizontal position" it is meant that when the support bar 8 is in its lower most position all of the parts depending therefrom are immersed in the liquid corrosive media 6. The support bar 8 may be constructed of a corrosion resistant stainless steel bar, circular in cross section. Alternatively, the support bar 8 may be of a variety of cross sectional shapes or configurations.

The parts 10–14 to be tested in the apparatus of the present invention typically include corrosion resistant materials, such as powder metal parts, made of stainless steel, superalloy powders and titanium metal powders, and a variety of plated parts or painted parts. These parts, or test specimens, usually have dimensions less than a few inches. However, parts having larger dimensions, such as welded pipe, may be tested in lengths as long as the inside lateral dimension of the apparatus provided that an appropriate reservoir may be provided.

Such parts 10–14 depend from the support bar 8 such that all parts hang at substantially the same level. In a preferred embodiment each part is hung from the support bar 8 with a glass rod 16 provided with a hooked portion 18 at each end thereof. Preferrably at least one hooked portion 18 of each glass holder 16 is provided with a contour that mates substantially with the exterior surface contour of the support bar 8. Also the support bar 8 may be provided with a series of indentations or ridges, not shown, into which the hooked portion 18 of the glass holder 16 may be held to minimize or to prevent lateral movement of the glass rods 16 and the parts hung therefrom during operation of the apparatus.

It will be understood that the part holding portion of the glass holders 16 may have to be provided with a plurality of contours, shapes and designs in order to accommodate a variety of shapes of parts to be tested. Also there may be parts such as discs, that cannot be held by a hooked portion and a basket type holder or clip may have to be provided on the part holding portion of such glass holder 16.

As an alternative to glass holders 16, threads or strands, of nonreactive, corrosion resistant fiberglass, nylon, polyethylene or the like may be used to tie the parts to be tested from the support bar 8. Also in certain instances when a plurality of parts are to be immersed into a common liquid bath such parts may be supported on a single holder 16. It should be noted that the supporting of a plurality of parts from a single holder should be avoided in instances where galvanic corrosion may occur and adversely affect the test results.

The support bar 8 is reciprocally moveable within the apparatus of the present invention. In a preferred embodiment the end portions of the support bar 8 which are located within the housing shown in the drawing are driven by a conventional, pneumatically operated piston cylinder assembly, not shown. In such embodiment at least one end of the support bar 8 is attached to the piston rod. If only one piston-cylinder assembly is used to move the support bar 8, a guide assembly 20 may have to be provided to assure that the bar 8 remains substantially in the horizontal position during operation. The preferred piston-cylinder assembly of this apparatus typically operates with an air supply of from 35 to 45 psi to maintain horizontal balance when using two piston-cylinder assemblies. When only one piston-cylinder assembly is used, an air supply in excess of about 160 psi should rarely be required. Further, it is preferred that double-cushion piston-cylinders be employed to absorb the last few increments of upward and downward movement of the support bar, so as not to jar the supported samples with abrupt stopping. A regulator may also be provided to maintain any desired pressure. It will be understood that alternative positioning devices such as a rack and pinion arrangement may be provided to reciprocally drive the bar 8.

Figure 2:
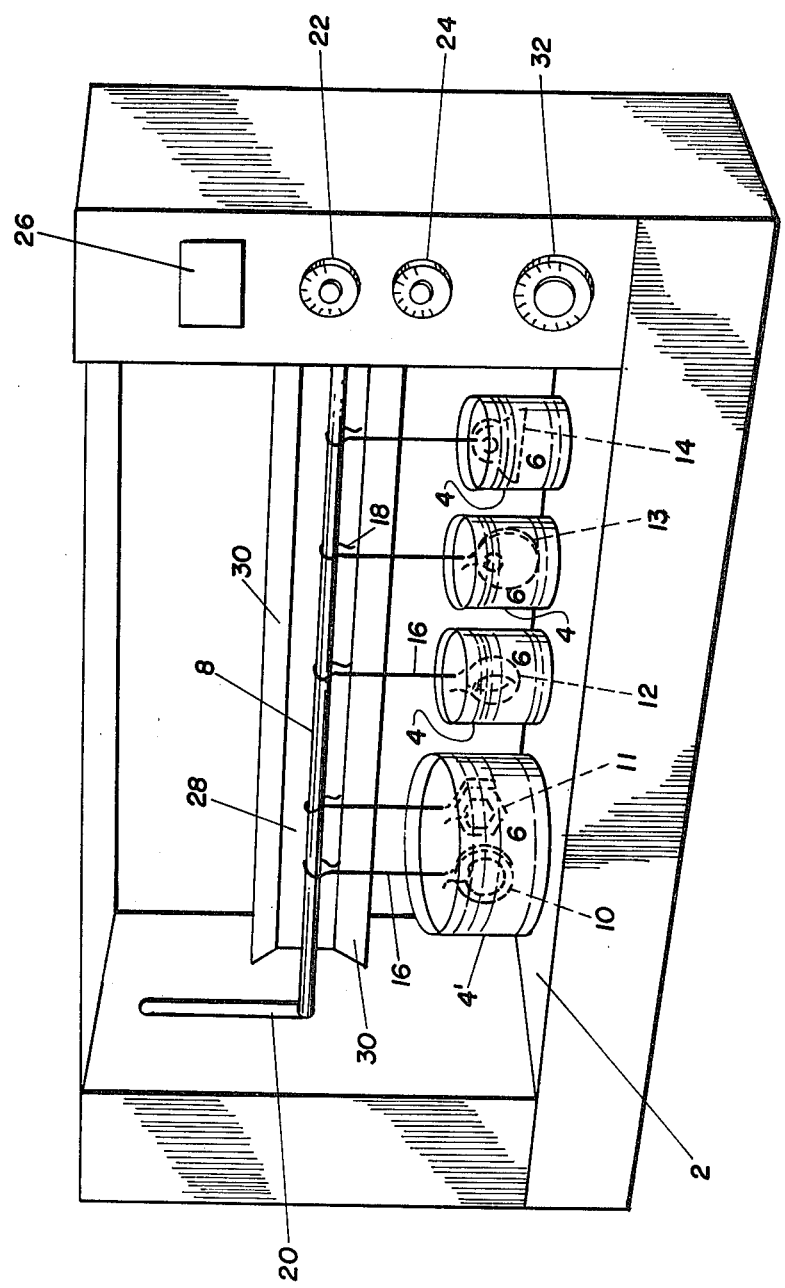
FIG. 2 is a perspective view of the apparatus of the present invention showing the parts immersed in the corrosive liquid media.

The bar 8 is positioned from its substantially uppermost position as shown in FIG. 1 to its substantially lowermost position as shown in FIG. 2. The elapsed time within which the bar 8 occupies each position must be precisely controllable to assure uniformity in the results obtained by testing with this apparatus. Therefore, a timer or a plurality of timers such a series CM4 industrial timer manufactured by Esterline Corporation, should be provided in the test apparatus of this invention. The controls 22 and 24 for such timers should be readily accessible preferably on the face of the housing for the test unit. Typically, the timer controls 22 and 24 are set such that the support bar 8 occupies its lowermost position for a relatively short period of time such as 1–5 seconds and its uppermost position for a longer period of time such as 30–120 seconds.

In a preferred embodiment a cam is provided on a rotating timer which repeats a continuous, adjustable, electrical cycle. The cam should also be adjustable to actuate a control, such a micro-switch, for any portion of the selected cycle time within two percent (2%) to ninety-eight percent (98%) thereof. By such mechanism the cam may be adjusted to control the amount of time that the supported parts are held in the drying zone before immersion into the corrosive bath. Such device may also control the time that the supported parts are held in the corrosive bath 6.

Another control measure that is preferably provided in the test apparatus of the present invention is a counter 26 such as is manufactured by Veederoot Company. The counter should be mounted such that it is visible on the face of the housing of the test apparatus to readily indicate the number of raising and lowering cycles through which the support bar 8 has passed during any one test. Considering that many of the accelerated corrosion tests require an elapsed time often in excess of eight hours, the counter 26 can serve as a check on the precision of the machine, and as a periodic indication of the status of the test.

As mentioned above, all of the parts depending from the support bar 8 are hung at substantially the same level. Such disposition of parts assures that all parts are immersed in the corrosive liquid when the support bar 8 is in its lowermost position as illustrated in FIG. 2. Additionally, the parts are hung at substantially the same level to assure that all parts are substantially centrally located in a temperature controlled drying zone when the bar 8 is in its uppermost position as illustrated in FIG. 1.

The drying zone is an area located substantially vertically above the reservoir 4 of corrosive liquid media 6 in which a controlled temperature of from room temperature to about 75° C. (170° F.) is maintained and controlled within a range of plus or minus 10° C. In order to accelerate corrosion of a part, that part may be repeatedly immersed in a corrosive media with an intermittent drying stage. The drying is accomplished in the preferred apparatus shown in the drawing by providing an electric heating element 28, such as a Brisket Heater, manufactured by Briscoe Manufacturing Company. This heater comprises an iron resistance wire embedded in silicon. Preferably a further external layer of adhesive silicon is applied to heating element 28 in order that the heater does not corrode in the testing environment. Such an arrangement provides a non-glowing heat assembly which is able to control the temperature in the drying zone within close tolerances. A heat reflecting element 30 preferably of stainless steel, is provided to direct the heat to a central location in the apparatus defining the drying zone. It should be understood that more than one heating element and reflector may be provided, such as oppositely disposed heaters on reflectors, centrally located to concentrate the heat of the drying zone into an area between the two heaters. The heating element 28 and reflector 30 are combined into a single unit for concentrating the heat in the drying zone in order to accelerate the drying process. Such heating combination should have the capability of controlling the temperature in the drying zone to within plus or minus 10° C., or preferably within plus or minus 2½° C. throughout a test. Accelerated corrosion tests for different parts have different test parameters, including the temperature at which the part should be dried. Often, drying time and temperature may be interrelated. Therefore, a heating control such as a temperature sensitive thermocouple should be provided in the test apparatus that is controllable by an external temperature selector 32. A thermometer may also be provided to measure and to display the actual temperature in the drying zone during operation of the apparatus.

In order to maintain rigid control of the testing procedure to eliminate variables which may be caused by changes in the ambient areas about the apparatus, a transparent cover should be provided over the face of the housing to enclose the working elements of the apparatus and thereby isolate the reservoir, heating zone and supported parts from the ambient surrounding. Such enclosed construction also economically retains heat in the drying zone and permits visual observance of the corrosion during the operation of the apparatus.

The apparatus of this invention is self-controlling during operation. Technically competent personnel are not required for the set up or operation of the unit. Once the solutions are prepared and the samples are supported from the bar 8 at substantially the same level, the unit is started and continuously operated without the need for monitoring. Furthermore, the apparatus should be provided with an automatic lock-out mechanism which stops the operation of the support bar and discontinues the elapsed timer and cycle counter simultaneously so as not to distort the results of an interrupted test.

In a typical operation of the test apparatus of the present invention, a corrosive test liquid must be prepared. A suitable solution for testing powder metal stainless steel parts is a 1% by weight aqueous sodium chloride (NaCl) solution. It should be noted that the present invention is adapted for testing a variety of parts in various acidic or basic solutions. Demineralized water and reagent chemicals should be used in preparing the solutions.

The drying zone in the unit should be preheated to the desired temperature. In the present example the drying zone is maintained at a temperature of about 50° C. (120° F.). The sample support bar should be locked in the uppermost position for part mounting. A plurality of specimens or parts are mounted to the support bar with a plurality of glass rods, preferably one specimen per rod. A 250 milliliter beaker is provided at the base of the unit vertically below each part supported from the bar. The beakers are filled with a corrosive liquid prior to positioning in the apparatus to avoid splashing of the parts or the apparatus prior to the operation of the unit.

A cycle time may be chosen such that the parts are fully immersed in the corrosive solution for one second and lifted to the drying zone for 100 seconds. Such parameters may be set on the timer controls. In a preferred apparatus the immersion and the drying times may be integrated into the operation of the unit in instances where the user does not contemplate the necessity of adjusting such times.

After the counter and elapsed timer controls are set to a zero or referenced position, the unit is started by activating the appropriate switch. No further monitoring is required. The apparatus operates to immerse the parts into the corrosive liquid for one second, lift the parts to a temperature controlled drying zone for 100 seconds and repeat that process as long as desired or required. Upon immersion of the parts into the corrosive bath, the bath constituents enter the pores of the immersed part, and the heat of the drying zone acts to concentrate the bath constituents in the pores. As the test proceeds, the concentration of the bath increases. A typical test lasts 270 cycles, or about eight hours. It will be understood that an automatic shut off mechanism may be provided to stop the operation of the apparatus after a certain elapsed time or after a certain number of cycles.

Whereas, the particular embodiments of this invention have been described above for purposes of illustration, it will be apparent to those skilled in the art that numerous variations of the details may be made without departing from the invention.

What is claimed is:

1. In an apparatus for accelerated testing of the corrosion resistance of a plurality of parts comprising:
   a support bar disposed substantially in the horizontal direction,
   means connected to the support bar for individually supporting each part to be tested in a position depending downwardly from the support bar, the supporting means being substantially corrosion resistant,
   a reservoir for holding a liquid corrosive media, the reservoir located vertically below the support bar and sized sufficient to allow immersion of each part depending from the support bar on the supporting means, the reservoir being substantially corrosion resistant, and
   means for repetitively raising and lowering the support bar in a vertical plane, while the support bar retains its horizontal disposition, such that all supported parts are immersed in the corrosive media for the same period of time each instance that the bar is moved to its lowermost position;
   the improvement comprising
   a drying zone located vertically above the reservoir,
   means for maintaining an elevated temperature within a range of from room temperature to about 75° C., in the drying zone, said temperature being controlled to within plus or minus 10° C. with a silicon coated heating element mounted on the inside surface, with respect to the test environment, of a stainless steel reflector,
   means for retaining all supported parts completely within the drying zone each instance that the support bar is moved to its uppermost position, and
   a housing, at least partially transparent, for isolating the test environment including the drying zone from the ambient surroundings.

* * * * *